United States Patent
Chang et al.

(10) Patent No.: US 8,372,392 B2
(45) Date of Patent: Feb. 12, 2013

(54) *LACTOBACILLUS PARACASEI* STRAIN LT12 AS IMMUNITY REGULATORY AGENT

(75) Inventors: William Tien Hung Chang, Taipei (TW); Yi Chieh Wang, Taipei (TW); Shu Ling Li, Taipei (TW)

(73) Assignee: Lytone Enterprise, Inc., Taipei (TW)

( * ) Notice: Subject to any disclaimer, the term of this patent is extended or adjusted under 35 U.S.C. 154(b) by 339 days.

(21) Appl. No.: 12/646,275

(22) Filed: Dec. 23, 2009

(65) Prior Publication Data

US 2011/0150838 A1    Jun. 23, 2011

(51) Int. Cl.
- C12N 1/21 (2006.01)
- C12N 1/20 (2006.01)
- A61P 37/08 (2006.01)
- A61P 37/02 (2006.01)

(52) U.S. Cl. ............ 424/93.45; 424/93.4; 435/471; 435/252.3; 435/252.9

(58) Field of Classification Search .............. None
See application file for complete search history.

(56) References Cited

U.S. PATENT DOCUMENTS

| | | | | |
|---|---|---|---|---|
| 2005/0214271 | A1* | 9/2005 | Hsu et al. | 424/93.45 |
| 2005/0220776 | A1* | 10/2005 | Brondstad et al. | 424/93.45 |
| 2006/0088513 | A1* | 4/2006 | Inoue et al. | 424/93.45 |

OTHER PUBLICATIONS

Greenspan et al. (Nature Biotechnology 7: 936-937, 1999).*

* cited by examiner

*Primary Examiner* — Robert A Zeman
(74) *Attorney, Agent, or Firm* — Occhiuti Rohlicek & Tsao LLP

(57) ABSTRACT

An isolated *Lactobacillus paracasei* strain LT12 and its genetically-engineered variant that possesses immune regulating activity and uses thereof for regulating immune responses and treating allergy.

5 Claims, 1 Drawing Sheet

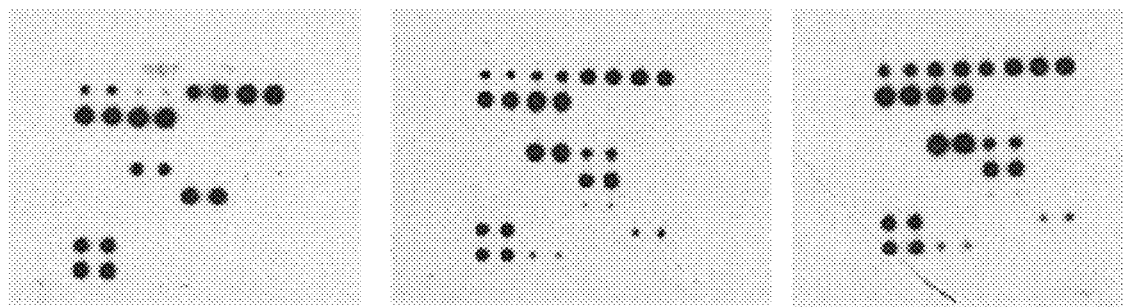
(A)　　　　　　　(B)　　　　　　　(C)
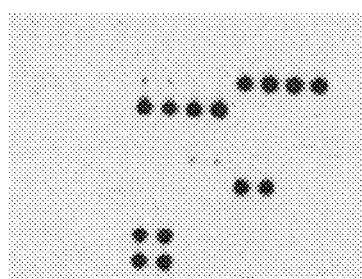　　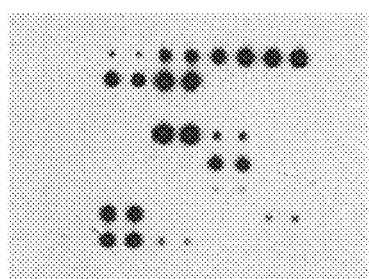
(D)　　　　　　　(E)

1

LACTOBACILLUS PARACASEI STRAIN LT12 AS IMMUNITY REGULATORY AGENT

FIELD OF THE INVENTION

The present invention is related to a novel *Lactobacillus paracasei* strain and its use for regulating immunity and treating allergy related disorder.

BACKGROUND OF THE INVENTION

Allergy refers to an exaggerated reaction by our immune system in response to certain foreign substances, i.e. bacteria, pollens, or dust, which are known as "allergen". These allergens are sometimes seen by the body as harmful and dangerous, and one part of immune system is turned on, while in reality they were not infectious or toxic. When an allergen comes in contact with the body and create an allergic reaction, histamine and prostaglandin may be released subsequently and generate allergic disorder including airway inflammation, atopic dermatitis, allergic conjuctivitis, urticaria, eczema, specific gastrointestinal disorders or asthma.

It is reported that children in developed countries are prone to having allergy because of improved public health and the use of vaccine and antibiotics decrease the incidences of infections which normally against allergy or asthma. In medicine, it is called "hygiene hypothesis" stated that a lack of early childhood exposure to infectious agents leads to Th-2 mediated immune response, i.e. the overproduction of IL-4, IL-5 and IL-13. These Th-2 cytokines attract eosinophils, basophils and mast cell to the inflammation site along or cooperatively working with IgE and allergy occurs. On the other hand, IL-4 and IL-13 stimulate B cells' isotype switching to increase the blood level of IgE. According to the hygiene hypothesis, upregulation of Th-1 response, i.e. stimulating the expression of IFN-$\gamma$, might be effective in inhibiting allergic activities.

Many searches show that *Lactobacillus* sp. have immunoregulating activities in vivo, including stimulating the expression of cytokines, activating macrophages and natural killer cells, and production of antibodies (Madsen et al., 2001, *Gastroenterology* 121:580-591). Collins et al. (U.S. Pat. No. 7,390,519) disclosed that *Lactobacillus salivarius* strains AH102, AH103, AH105, AH109 or AH110 are useful in the prophylaxis and/or treatment of inflammatory activity as anti-inflammatory biotherapeutic agents. Hsu et al. (U.S. Pat. No. 6,994,848) discloses that a *Lactobacillus paracasei* strain, GM-080, stimulates IFN-$\gamma$ secretion and treating allergy related diseases.

However, the effects of lactic acid bacteria isolated from various natural sources have not been thoroughly researched and fully discovered. The present invention provides a composition containing such a novel strain of *Lactobacillus paracasei* and its use for immunoregulating activities, which are different from related prior art strains, are disclosed.

BRIEF SUMMARY OF THE INVENTION

In one aspect, the present invention provides a novel *Lactobacillus paracasei* strain LT12 having immunoregulating activity (e.g., anti-allergy activity) or its genetically-engineered variant, which is a *Lactobacillus paracasei* strain prepared by introducing an exogenous gene into LT12 via genetic engineering. In one example, the variant is produced by the following steps: (i) providing a cell of LT12, and (ii) introducing into the cell an expression cassette in which an exogenous gene is operably linked to a promoter.

In another aspect, this invention features a composition containing the above-mentioned *Lactobacillus paracasei* strain LT12 or its variant and a carrier. The composition can be a food product (e.g., yogurt, cookies, cereals, chocolates, and snack bars), a drink (e.g., tea, soft drink, milk, and juice), or a medicament containing a pharmaceutically acceptable carrier.

In yet another aspect, the invention features a method for regulating immunity (i.e., innate immunity or adaptive immunity) or for treating allergy by administering to a subject in need thereof an effective amount of any of the compositions mentioned above. The subject can be a patient (e.g., a human patient) suffering from IgE-mediated immediate hypersensitivity or T-cell-mediated delayed hypersensitivity.

Also within the scope of this invention is use of the *Lactobacillus paracasei* strain LT12 mentioned above in manufacturing a medicament for regulating immunity or treating allergy.

The details of one or more embodiments of the invention are set forth in the description below. Other features or advantages of the present invention will be apparent from the following drawings and detailed description of several embodiments, and also from the appending claims.

BRIEF DESCRIPTION OF THE DRAWINGS

The foregoing summary, as well as the following detailed description of the invention, will be better understood when read in conjunction with the appended drawings. It should be understood, however, that the invention is not limited to the precise arrangements and instrumentalities shown.

In the drawings:

FIG. 1 are photos showing the blots of Human cytokine antibody array on each group: PBMCs source C blank group (FIG. 1A), PBMCs source C stimulated by LT12 alone (FIG. 1B), PBMCs source C stimulated by LT12 combined with second *Lactobacillus paracasei* (FIG. 1C), PBMCs source E blank group (FIG. 1D), and PBMCs source E stimulated by LT12 (FIG. 1E). The cytokine antibody array map on the membrane was shown as Table V.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference.

DETAILED DESCRIPTION OF THE INVENTION

This present invention provides a novel strain of *Lactobacillus paracasei*, called as strain LT12 (hereafter "LT12"), which is capable of regulating immunity and treating allergy. The strain LT12 was deposited under the Budapest Treaty on Sep. 21, 2009 with the Agricultural Research Culture Collection, International Depositary Authority, 1815 N. University Street, Peoria, Ill., 61601, U.S.A. and has been assigned a deposit number NRRL-B50327.

*Lactobacillus paracasei* strain LT12 was isolated from human feces. Processing of fecal samples occurred within 12 hours after collection. Weighted samples (about 1 g) were homogenized for 30 sec in a stomacher (Stomacher 400, Seward, UK) before dilution in a pre-reduced brain hearth infusion broth and cultivation on the appropriate selective media. Appropriate dilutions were plated using Rogosa Acetate agar (Difco, USA) and Rogosa Acetate agar (Difco, USA) added with 12 µg/ml of vancomycin (Sigma, USA) to enumerate total *Lactobacillus* spp. and vancomicyn insensitive lactobacilli (i.e. *L. paracasei* group, including *L. paracasei, L. casei* and *L. rhamnosus*), respectively. API 50 CHL (bioMérieux, Inc. USA) was performed to identify species among the vancomycin-insensitive *L. paracasei* group, and the results were listed in Table I.

The microbiological characteristics of the LT12 are shown below:
(1) Morphological Characteristics:
   (a) Shape and size of cell: The bacteria has a rod-like shape with round edge when culturing at 37° C. overnight in MRS broth observed by microscope.
   (b) Motility: motile
   (c) Flagella: none
   (d) Sporulation: no spore-forming
   (e) Gram-stain: positive
(2) Cultural Characteristics:
   (a) Medium: lactobacillus MRS broth (Difco, USA), final pH 6.2-6.5
   (b) Cultural condition: 37° C., anaerobic or aerobic culture
(3) Physiological Characteristics:
   (a) Catalase: positive
   (b) Oxidase: negative
   (c) API 50 CHL test: The result is listed in Table 1.
(4) Genetic Characteristics:

As shown in Example 2, randomly amplified polymorphic DNA (RAPD analysis) was performed on LT12, *Lactobacillus paracasei* (Cell biotech Co., Ltd., Korea, "LP-CBT"), *Lactobacillus paracasei* GMNL32 ("GMNL32"), *Lactobacillus paracasei* subsp. *paracasei* BCRC 14023 ("BCRC14023") and *Lactobacillus paracasei* subsp. *paracasei* BCRC 12188 ("BCRC 12188"). Twelve random primers were chosen and listed in Table II. The electrophoresis results showed that LT12 had different bands pattern (as shown in Table III). Given above, LT12 is a novel *Lactobacillus paracasei* strain.

Also disclosed herein are genetically-engineered LT12 variants prepared by introducing one or more suitable exogenous genes into LT12. Such variants can be prepared by standard techniques in molecular biology. For example, cells of LT12 can be cultured under suitable conditions and an exogenous gene of interest, operably linked to a suitable promoter, can be introduced into the LT12 cells via a routine transformation method, e.g., electrotransformation as described in openwetware.org/wiki/*Lactobacillus*_transformation. Positive transformants can then be identified and expression of the exogenous gene can be confirmed by examining the protein level of the gene product via, e.g., ELISA or Westernblot, or by examining the activity of the gene product via a suitable assay. A promoter sequence is a nucleotide sequence containing an element(s) necessary for initiating transcription of an operably linked nucleic acid sequence. At a minimum, a promoter contains an RNA polymerase binding site. It can further contain one or more enhancer elements that enhance transcription, or contain one or more regulatory elements that control the on/off status of the promoter. Examples of the exogenous gene include, but are not limited to, a gene encoding an immune regulator (e.g., a cytokine or a superantigen), a gene encoding a therapeutic protein, or a gene encoding a protein that facilitates *Lactobacillus paracasei* growth.

According to one embodiment of the invention, the strain LT12 or its variant may be used in the form of viable cells. In another embodiment of the invention, they may be non-viable cells such as a heat-killed culture containing the beneficial factors produced by strain LT12.

The present invention provides strain LT12 or its genetically-engineered variant having immunoregulating activities and/or anti-allergic activities. The term "immunoregulating activity" refers to the function of activating a steady or depressed immune function (immunostimulating activity), or the function of suppressing an excess or over-reacted immune function to an appropriated level (immunosuppressing activity). In other word, it is to control the immune cells (i.e. T cells, B cells, macrophages) to stabilize overall balance of the immune response. For examples, but not limited to, stimulating or suppressing cytokine production, activating lymphocytes, balancing Th1/Th2 activities and inhibiting allergic activities.

The present invention also provides strain LT12 or its variant being capable of treating allergy. The term "allergy" refers to an immune response that is harmful to the host from a physiological state of protective immunity. The most common form of allergy is caused by IgE-mediated immediate hypersensitivity, and T cell-mediated delayed hypersensitivity. The allergic activities manifest clinically as allergic rhinitis, allergic asthma, food allergy, allergic skin inflammation, ocular allergy and anaphylaxis. The term "treating allergy" refers to stimulate a series of immune activities which might reverse the allergic symptoms described above, for example, but not limited to, blocking the Th-2 mediated immunity, decreasing the production of Th-2 mediated cytokines (i.e., IL-4, IL-5, IL-13), increasing Th-1 mediated cytokines (i.e., INF-γ), and preventing the activation or differentiation of IgE$^+$ memory B cells and eosinophils.

In one embodiment of the present invention, LT12 was capable of stimulating peripheral blood mononuclear cells (PBMCs) isolated from volunteers to secret INF-γ, as demonstrated by ELISA (shown in Table IV). INF-γ is a cytokine that is critical for innate and adaptive immunity against viral and intracellular bacterial infections. It is the hallmark cytokine of Th1 cells and inhibits Th-2 cells differentiation therefore decrease the production of IL-4, IL-5, IL-13, which induce immunoglobulin class-switching to IgE and clonal expansion of naive and IgE$^+$ memory B cell population. Accordingly, stimulating the expression of IFN-γ might be effective in treating allergy.

In another embodiment of the present invention, LT12 was also capable of stimulating peripheral blood mononuclear cells (PBMCs) secretion of other cytokines, comprising IL-1α, IL-6, IL-10, IFN-γ, MCP-2, and TNF-α determined by Human cytokine antibody array (as shown in FIG. 1A-1E and Table VI).

Accordingly, the present invention provides a method for a method for regulating immunity comprising administering to a subject in need thereof a composition comprising an effective amount of *Lactobacillus paracasei* strain LT12 and a pharmaceutically acceptable carrier thereof.

The present invention also provides a method for treating allergy comprising administering to a subject in need thereof a composition comprising an effective amount of *Lactobacillus paracasei* strain LT12 and a pharmaceutically acceptable carrier thereof. The term "pharmaceutically acceptable carrier" as used herein may include, but not limited to: saline, buffered saline, dextrose, water, glycerol, ethanol and combinations thereof.

Unexpectedly, the present invention further discovers a composition containing LT12 and a second strain of *Lactobacillus paracasei* having immunoregulating activities and/or anti-allergy activities. In one embodiment, the second strain of *Lactobacillus paracasei* is LP-CBT and the ratio of LT12 to the second strain is 100:1 by bacterial number. Preferably, the ratio of the LT12 to the second strain is 2:1. As shown the results in Example 4, the combined composition was also capable of stimulating peripheral blood mononuclear cells (PBMCs) secretion of other cytokines, comprising IL-1α, IL-6, IL-10, IFN-γ, MCP-2, and TNF-α determined by Human cytokine antibody array. Moreover, MCP-3 merely expressed in PBMCs stimulated by LT12 combined composition.

According to the invention, the strain LT12 provides excellent immunoregulating and anti-allergy activity. In one example of the invention, the strain LT12 or its combination can be used as an active ingredient in a composition. The composition can be manufactured as food, a drink or a medicament. In addition, a variety of additives can be included.

EXAMPLE 2

Characterization of *Lactobacillus paracasei* Strain LT12

Species Identification

API 50 CHL system is used for identification of lactic acid bacteria. By assaying the responses of a serious of enzymes, the characters of the lactic acid are established. The result of API 50 CHL test of LT12 is listed in Table I.

TABLE I

API 50 CHL test of LT12
Reference: LT12
VERY GOOD IDENTIFICATION TO THE GENUS
Strip: API 50 CHL V5.1
Profile: -----+----+++++-++++-+++++++++-+++----+++----+--

| CTRL | - | GLY | - | ERY | - | DARA | - | LARA | - | RIB | + | DXYL | - | LXYL | - | ADO | - | MDX | - |
| GAL | + | GLU | + | FRU | + | MNE | + | SBE | + | RHA | - | DUL | + | INO | + | MAN | + | SOR | + |
| MDM | - | MDG | + | NAG | + | AMY | + | ARB | + | ESC | + | SAL | + | CEL | + | MAL | + | LAC | + |
| MEL | - | SAC | + | TRE | + | INU | + | MLZ | + | RAF | - | AMD | - | GLYG | - | XLT | - | GEN | + |
| TUR | + | LYX | + | TAG | + | DFUC | - | LFUC | - | DARL | - | LARL | - | GNT | + | 2LG | - | 5KG | - |

| | % Id. | T value | Test against |
|---|---|---|---|
| Significant Test | | | |
| *Lactobacillus paracasei* ssp *paracasei* 1 | 95.2% | 0.69 | DUL 13% INO 6% LYX 20% |
| Next Choice | | | |
| *Lactobacillus paracasei* ssp *paracasei* 2 | 4.6 | 0.6 | LAC 0% LYX 16% |

Examples of additives include but are not limited to colorings (e.g., beta-carotene, anatto, tumeric, paprika and FD & C dyes); flavors, aromas, sweeteners; emulsifiers and/or thickening agents; preservatives, vitamins and antioxidants (e.g., vitamins A, C, D, E, B-1, B-5, B-6, zinc, selenium, calcium, alpha-tocopherol, glutathione, butylated hydroxytoluene (BHT), butylated hydroxyanisole (BHA), and cysteine).

The present invention is further illustrated by the following examples, which are provided for the purpose of demonstration rather than limitation.

EXAMPLE 1

Isolation of *Lactobacillus paracasei* Strain LT12

*Lactobacillus paracasei* strain LT12 was isolated from human feces. Processing of fecal samples occurred within 12 hours after collection. Weighted samples (about 1 g) were homogenized for 30 sec in a stomacher (Stomacher 400, Seward, UK) before dilution in a pre-reduced brain hearth infusion broth and cultivation on the appropriate selective media. Appropriate dilutions were plated using Rogosa Acetate agar (Difco, USA) and in which added with 12 μg/ml of vancomycin (Sigma, USA) to enumerate total *Lactobacillus* spp. and vancomycin insensitive lactobacilli (i.e. *L. paracasei* group, including *L. paracasei, L. casei* and *L. rhamnosus*), respectively. API 50 CHL (bioMerieux, Inc. USA) was performed to identify species among the vancomycin-insensitive *L. paracasei* group.

Random Amplification of Polymorphic DNA (RAPD Analysis)

DNA extraction of LT12, *Lactobacillus paracasei* (Cell biotech Co., Ltd., Korea, "LP-CBT"), *Lactobacillus paracasei* GMNL32 ("GMNL32"), *Lactobacillus paracasei* subsp. *paracasei* BCRC 14023 ("BCRC 14023") and *Lactobacillus paracasei* subsp. *paracasei* BCRC 12188 ("BCRC 12188") following 40 hrs cultivation were conducted for RAPD analysis by twelve random primers listed as Table II. The results of RAPD were shown in Table III, LT-12 was observed different bands pattern compared to the other four strains by electrophoresis.

According to API 50 CHL identification and RAPD analysis, LT12 was distinct from the conventional *Lactobacillus paracasei* strains. Given the above, LT12 was a novel *Lactobacillus paracasei* strains.

TABLE II

| Code | Sequence (5'-3') | SEQ ID NO | FIG. |
|---|---|---|---|
| OPD-01 | ACCGCGAAGG | 1 | 1A |
| OPD-03 | GTCGCCGTCA | 2 | 1B |
| OPD-07 | TTGGCACGGG | 3 | 1C |
| OPD-20 | ACCCGGTCAC | 4 | 1D |
| OPS-03 | CAGAGGTCCC | 5 | 1E |
| OPS-07 | TCCGATGCTG | 6 | 1F |
| OPS-10 | ACCGTTCCAG | 7 | 1G |

TABLE II -continued

| Code | Sequence (5'-3') | SEQ ID NO | FIG. |
|---|---|---|---|
| OPS-11 | AGTCGGGTGG | 8 | 1H |
| OPS-12 | CTGGGTGAGT | 9 | 1I |
| OPS-13 | TGGGGACCAC | 10 | 1J |
| OPS-17 | TGGGGACCAC | 11 | 1K |
| OPS-19 | GAGTCAGCAG | 12 | 1L |

TABLE III

|  | LP-CBT | GMNL-32 | BCRC 14023 | BCRC 12188 |
|---|---|---|---|---|
| OPD-01 | ○ | — | — | ○ |
| OPD-03 | ○ | — | — | — |
| OPD-07 | ○ | ○ | — | ○ |
| OPD-20 | ○ | ○ | ○ | — |
| OPS-03 | ○ | ○ | — | ○ |
| OPS-07 | — | ○ | — | — |
| OPS-10 | ○ | ○ | ○ | ○ |
| OPS-11 | — | ○ | — | — |
| OPS-12 | — | ○ | ○ | — |
| OPS-13 | ○ | ○ | ○ | ○ |
| OPS-17 | ○ | ○ | ○ | ○ |
| OPS-19 | ○ | ○ | — | ○ |
| Distinct No. | 9 | 10 | 5 | 7 |

Note:
○ referred to distinctive primer, while — referred to indistinctive primer

EXAMPLE 3

Activities of LT12 and Other Lactic Acid Bacteria in Regulating Allergy

Preparation of Bacteria

LT12, LP-CBT and Lactobacillus rhamnosus GG (hereafter "LGG") were cultured in lactobacillus MRS broth at 37° C. for 24 hours, and collected by centrifuging at 3000 rpm for 15 minutes. The pellet was washed twice with 1 ml PBS (phosphate buffered saline) and then heated at 95° C. for 30 minutes to obtain heat-killed bacteria preparations.

Isolation of Peripheral Blood Mononuclear Cells

Fresh blood samples derived from healthy volunteers (two males, three females, between 24-40 years old) were centrifuged at 2000 rpm for 10 minutes under room temperature, and then collected the samples from buffy coat layer. The collections were added with the equal volume of dilute medium (RPMI-1640 plus 2% fetal bovine serum (FBS)) and then slowly removed to 4 ml Histopaque-1077 ficoll plus solution. The peripheral blood mononuclear cells (PBMCs) were taken from the interface of the samples following centrifuging at 1200 rpm for 30 minutes, and washed twice with 8 ml wash medium (RPMI-1640 plus 2% FBS and 1% PBS (phosphate buffer saline)). The PBMCs ($10^6$ cells/ml) were transferred to the wells of a 24 well plate cultured with complete medium (RPMI-1640 plus 10% FBS and 1% PBS).

Stimulation IFN-γ Secretion and Determine of IFN-γ Level

The PBMCs samples were co-cultured with a given amount ($5\times10^6$, $5\times10^7$ or $5\times10^8$ CFU/ml) of LT12, LP-CBT and LGG. After 48 hours of co-culture, the supernatant in each well were collected for determining IFN-γ level by ELISA, comprising the steps below. 5 μg/ml PHA (phytohemagglutinin) and 10 μg/mlLPS (lipopolysaccharides) were used as positive control.

Adding 100 μl/well (96-well plate) of 4 μg/ml anti-IFN-γ antibodies (RayBio® Human IFN-γ ELISA, RayBiotech Inc., USA) overnight at 4° C. Washing each well with 250 μl wash buffer five times. Adding 200 μl/well of assay diluent and reacting for 1 hour at room temperature. Washing each well with 250 μl wash buffer five times and adding each well with 100 μl/ml of the supernatant of the PMBCs sample for 2 hours of reaction at room temperature. Was hing each well with 250 μl wash buffer five times and adding each well with 100 μl/well detection antibody for 1 hour. Washing each well with 250 μl wash buffer five times and adding each well with 100 μl/well Avidin-HRP (1:250) for 30 minutes. Washing each well with 250 μl wash buffer seven times and adding each well with 100 μl/well substrate solution. After incubation for three to fifteen minutes, 50 μl/well of 2N $H_2SO_4$ was added to stop the reaction. Measuring the absorbance of each well of the plate at 450 nm. The concentration of IFN-γ level was converted and calculated from a standard curve. The results were shown as Table IV.

Among the bacteria, LT12 had the strongest ability to stimulate IFN-γ secretion in different CFU group.

TABLE IV

| Test Sample | Bacteria Concentration (CFU/mL) | A | B | C | D | E | AVG ± SD |
|---|---|---|---|---|---|---|---|
|  |  | \multicolumn{5}{c}{IFN-γ (pg/mL)} |  |  |
| LT12 | $5*10^6$ | 7822 | 756 | 4717 | 3 | 1991 | 3058 ± 3210 |
|  | $5*10^7$ | 11058 | 9981 | 32180 | 236 | 11439 | 12979 ± 11685 |
|  | $5*10^8$ | 4507 | 8397 | 14169 | 4109 | 15079 | 9252 ± 5192 |
| LGG | $5*10^6$ | 2197 | 91 | 1036 | 15 | 293 | 726 ± 916 |
|  | $5*10^7$ | 5884 | 2562 | 14595 | 96 | 3399 | 5307 ± 5589 |
|  | $5*10^8$ | 1643 | 1326 | 2313 | 1399 | 1424 | 1621 ± 404 |
| LP-CBT | $5*10^6$ | 2273 | 81 | 456 | 2 | 74 | 577 ± 965 |
|  | $5*10^7$ | 6916 | 1623 | 3904 | 31 | 2010 | 2897 ± 2636 |
|  | $5*10^8$ | 11261 | 7188 | 8956 | 221 | 3181 | 6162 ± 4445 |
| Positive Control |  |  |  |  |  |  |  |
| PHA | 5 μg/mL | 15533 | 733 | 361 | 289 | 170 | 3417 ± 6776 |
| LPS | 10 μg/mL | 119 | 30 | 8 | 87 | 44 | 57 ± 45 |
| Negative Control |  |  |  |  |  |  |  |
| PBS |  | — | 0 | 0 | 7 | 4 | 3 ± 3 |
| Medium |  | 0 | 0 | 5 | 5 | 2 | 3 ± 3 |

EXAMPLE 4

Determination of the Effects of LT12 and its Composition on PBMCs Cytokine Production Heat-killed LT12 and LT12 composition including LT12 and LP-CBT in a ratio of 2:1 by bacteria numbers were prepared as the method disclosed above. RayBio® Human cytokine antibody array (Cat. AAH-CYT-1, RayBiotech Inc., USA) was used for determining the cytokine expression profile on PBMCs (source C and source E) co-cultured with LT12 ($5 \times 10^7$/ml) and LT12 composition ($5 \times 10^7$/ml) or 48 hours.

The array protocol was followed the manufacturing manuscript along with the kit (http://www.raybiotech.com/cytokine_antibody_array.asp). Briefly, using flat-tip tweezers to remove each membrane to be used from between the protective sheets and place in a well of the 8-well plate. Adding 2 ml/well blocking buffer, and shaking the plate for 30 minutes incubation. Aspirating the blocking buffer from the well and adding 1 ml/well sample. After shaking the plate for 2 hours of incubation, washing each well with 2 ml washing buffer I twice and then with 2 ml washing buffer II three times. Adding 1 ml/well Biotin-Antibody solution, and then shake the plate for 2 hours of incubation. Following aspirating the antibody solution, washing each well with 2 ml washing buffer I twice and then with 2 ml washing buffer II three times. Adding 2 ml/well HRP-Streptavidin solution, and then shaking the plate for 2 hours of incubation. Using tweezers to drip away the liquid on the membrane, and then putting it back onto the well. Adding 0.5 ml/well mixed detection buffer, and then incubating for 2 minutes away from light. Carefully removing each membrane from the plate and placing it on a plastic sheet protector or plastic wrap. The wrapped membrane in a film cassette was exposed to X-ray for 40 seconds. The cytokine antibody array map on the membrane was shown as Table V.

TABLE V

Cytokine Antibody Array Map

| GRO-α | GRO-α | IL-10 | IL-10 | RANTES | RANTES | Pos | Pos |
|---|---|---|---|---|---|---|---|
| GRO | GRO | IL-8 | IL-8 | MIG | MIG | Blank | Blank |
| GM-CSF | GM-CSF | IL-7 | IL-7 | MCP-3 | MCP-3 | Blank | Blank |
| GCSF | GCSF | IL-6 | IL-6 | MCP-2 | MCP-2 | Blank | Blank |
| Neg | Neg | IL-5 | IL-5 | MCP-1 | MCP-1 | Blank | Blank |
| Neg | Neg | IL-3 | IL-3 | IFN-γ | IFN-γ | TNF-β | TNF-β |
| Pos | Pos | IL-2 | IL-2 | IL-15 | IL-15 | TNF-α | TNF-α |
| Pos | Pos | IL-1α | IL-1α | IL-13 | IL-13 | TNF-β1 | TNF-β1 |

The results were shown in 1A-E and Table VI. The array test was divided into five groups: blank group (FIG. 1A), LT12 co-culture group (FIG. 1B), and LT12 composition co-culture group (FIG. 1C) of PBMC from source C, and blank group (FIG. 1D) and LT12 co-culture group (FIG. 1E) of PBMC from source E. Both co-culture groups were observed an increase of cytokine level, including IL-1α, IL-6, IL-10, IFN-γ, MCP-2 and TNF-α. Among these cytokines, IL-1α, IFN-γ, MCP-2 and TNF-α only expressed in PBMCs stimulated by LT12 or LT12 composition. When comparing the internal group within PBMCs from source C, it was shown that the expression level of GRO-α, IL-10 and MCP-2 stimulated by LT12 composition was higher than those by LT12 along. Moreover, MCP-3 merely expressed in PBMCs stimulated by LT12 composition.

TABLE VI

| | PBMCs from source C[a] | | PBMCs from source E[a] |
|---|---|---|---|
| Cytokines | ($5*10^7$)-LT12 | ($5*10^7$)-LT12 composition | ($5*10^7$)-LT12 |
| GCSF | 0 | 0 | 0 |
| GM-CSF | 0 | 0 | 0→+ |
| GRO | ≈ | ≈ | ≈ |
| GRO-α | ≈ | + | + |
| IL-1α | 0→+ | 0→+ | 0→+ |
| IL-2 | 0 | 0 | 0 |
| IL-3 | 0 | 0 | 0 |
| IL-5 | 0 | 0 | 0 |
| IL-6 | ++ | ++ | ++ |
| IL-7 | 0 | 0 | 0 |
| IL-8 | ≈ | ≈ | + |
| IL-10 | + | ++ | ++ |
| IL-13 | 0 | 0 | 0 |
| IL-15 | 0 | 0 | 0 |
| IFN-γ | 0→+ | 0→+ | 0→+ |
| MCP-1 | ≈ | ≈ | ≈ |
| MCP-2 | 0→+ | 0→++ | 0→+ |
| MCP-3 | 0 | 0→+ | 0 |
| MIG | 0 | 0 | 0 |
| RANTES | ≈ | ≈ | ≈ |
| TGF-β1 | 0 | 0 | 0 |
| TNF-α | 0→+ | 0→+ | 0→+ |
| TNF-β | 0 | 0 | 0 |

[a]The data was derived from a comparison result between the test groups and its blank group.
[b]0: no blot appeared on the membrane
≈: no difference
+: increase
++: much increase
0→+: the blot only appeared in the test groups It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

We claim:

1. An isolated *Lactobacillus paracasei* strain, wherein the *Lactobacillus paracasei* strain is LT12 deposited with the Agricultural Research Culture Collection as Deposit Number NRRL-B50327.

2. A composition comprising the *Lactobacillus paracasei* strain LT12 of claim 1.

3. The composition of claim 2, wherein the *Lactobacillus paracasei* LT12 strain is viable.

4. The composition of claim 2, wherein the *Lactobacillus paracasei* strain LT12 is inactivated.

5. The composition of claim 2, which is a food product, a drink, or a medicament.

* * * * *

SEQUENCE LISTING

<160> NUMBER OF SEQ ID NOS: 12

<210> SEQ ID NO 1
<211> LENGTH: 10
<212> TYPE: DNA
<213> ORGANISM: Artificial Sequence
<220> FEATURE:
<223> OTHER INFORMATION: Synthetic primer

<400> SEQUENCE: 1
accgcgaagg                                                          10

<210> SEQ ID NO 2
<211> LENGTH: 10
<212> TYPE: DNA
<213> ORGANISM: Artificial Sequence
<220> FEATURE:
<223> OTHER INFORMATION: Synthetic primer

<400> SEQUENCE: 2
gtcgccgtca                                                          10

<210> SEQ ID NO 3
<211> LENGTH: 10
<212> TYPE: DNA
<213> ORGANISM: Artificial Sequence
<220> FEATURE:
<223> OTHER INFORMATION: Artificial primer

<400> SEQUENCE: 3
ttggcacggg                                                          10

<210> SEQ ID NO 4
<211> LENGTH: 10
<212> TYPE: DNA
<213> ORGANISM: Artificial Sequence
<220> FEATURE:
<223> OTHER INFORMATION: Synthetic primer

<400> SEQUENCE: 4
acccggtcac                                                          10

<210> SEQ ID NO 5
<211> LENGTH: 10
<212> TYPE: DNA
<213> ORGANISM: Artificial Sequence
<220> FEATURE:
<223> OTHER INFORMATION: Synthetic primer

<400> SEQUENCE: 5
cagaggtccc                                                          10

<210> SEQ ID NO 6
<211> LENGTH: 10
<212> TYPE: DNA
<213> ORGANISM: Artificial Sequence
<220> FEATURE:
<223> OTHER INFORMATION: Synthetic primer

<400> SEQUENCE: 6
tccgatgctg                                                          10

<210> SEQ ID NO 7
<211> LENGTH: 10
<212> TYPE: DNA

-continued

```
<213> ORGANISM: Artificial Sequence
<220> FEATURE:
<223> OTHER INFORMATION: Synthetic primer

<400> SEQUENCE: 7
accgttccag                                                          10

<210> SEQ ID NO 8
<211> LENGTH: 10
<212> TYPE: DNA
<213> ORGANISM: Artificial Sequence
<220> FEATURE:
<223> OTHER INFORMATION: Synthetic primer

<400> SEQUENCE: 8
agtcgggtgg                                                          10

<210> SEQ ID NO 9
<211> LENGTH: 10
<212> TYPE: DNA
<213> ORGANISM: Artificial Sequence
<220> FEATURE:
<223> OTHER INFORMATION: Synthetic primer

<400> SEQUENCE: 9
ctgggtgagt                                                          10

<210> SEQ ID NO 10
<211> LENGTH: 10
<212> TYPE: DNA
<213> ORGANISM: Artificial Sequence
<220> FEATURE:
<223> OTHER INFORMATION: Synthetic primer

<400> SEQUENCE: 10
tggggaccac                                                          10

<210> SEQ ID NO 11
<211> LENGTH: 10
<212> TYPE: DNA
<213> ORGANISM: Artificial Sequence
<220> FEATURE:
<223> OTHER INFORMATION: Synthetic primer

<400> SEQUENCE: 11
tggggaccac                                                          10

<210> SEQ ID NO 12
<211> LENGTH: 10
<212> TYPE: DNA
<213> ORGANISM: Artificial Sequence
<220> FEATURE:
<223> OTHER INFORMATION: Synthetic primer

<400> SEQUENCE: 12
gagtcagcag                                                          10
```